United States Patent [19]

Snodgrass et al.

[11] Patent Number: 5,252,457
[45] Date of Patent: Oct. 12, 1993

[54] WASH COMPOSITION CONTAINING SIGNAL STOP REAGENT, TEST KIT AND METHOD OF USE WITH PEROXIDASE-LABELED SPECIFIC BINDING LIGAND

[75] Inventors: Gary L. Snodgrass, Batavia; Lisa D. Sprague, Holcomb; Harold C. Warren, III, Rush; Douglas R. Jones, Fairport; Thomas R. Kissel, Rochester, all of N.Y.

[73] Assignee: Eastman Kodak Company, Rochester, N.Y.

[21] Appl. No.: 773,065

[22] Filed: Oct. 8, 1991

[51] Int. Cl.$^5$ .............. G01N 33/535; G01N 33/543; G01N 33/569
[52] U.S. Cl. ......................................... 435/5; 435/7.2; 435/7.32; 435/7.34; 435/7.92; 435/28; 435/184; 435/963
[58] Field of Search ............ 435/5, 7.2, 7.32, 7.92, 435/28, 184, 962, 963, 968, 975, 7.34; 252/551

[56] References Cited

U.S. PATENT DOCUMENTS

| | | | |
|---|---|---|---|
| 3,427,381 | 2/1969 | Kirkland | 424/54 |
| 3,480,392 | 11/1969 | Carlos | 23/190 |
| 4,661,342 | 4/1987 | Yamazaki et al. | 424/54 |
| 4,824,784 | 4/1989 | Cantarow | 435/7 |
| 4,847,199 | 7/1989 | Snyder et al. | 435/36 |
| 4,948,726 | 8/1990 | Longoria | 435/7 |
| 4,965,191 | 10/1990 | Warren, III et al. | 435/7 |
| 5,017,474 | 5/1991 | McClune et al. | 435/7 |

FOREIGN PATENT DOCUMENTS 0328388 12/1988 European Pat. Off.
205001 3/1982 Fed. Rep. of Germany.
54-141763 9/1979 Japan.

OTHER PUBLICATIONS

Schonbaum, *J. Biol. Chem.*, 248(2), 502–511, 1973.
Brooks, *Biochem..Biophys. Res. Comm.*, 116(3), 916–921 (1983).
Nakatani et al, *Biochem.* 25, 3515–3518 (1986).
Ator et al., *J. Biol. Chem.*, 262(4), 1542–1551 (1987).
Rich et al., *Biochim. Biophys. Acta*, 525, 325–337 (1978).
Ikeda-Saito et al, *J. Biol. Chem.*, 266(6), 3611–3616 (1991).
Aviram, *Arch. Biochem. Biophys.*, (212(2), 483–490 (1981).
Persijn et al *J. Clin. Chem. Clin. Biochem.* 16 (1978) 531–532.
Davies et al. Biochem. J. (1989) 258 801–806.

Primary Examiner—Esther L. Kepplinger
Assistant Examiner—Lora Marie Green
Attorney, Agent, or Firm—J. Lanny Tucker

[57] ABSTRACT

A buffered composition containing a nonionic or anionic surfactant, and a certain amount of a hydroxamic acid (or salt thereof) or an acyl hydrazine can be used as a wash composition in specific binding assays. Such assays include the use of a peroxidase labeled specific binding reactant to form a detectable peroxidase-labeled specific binding complex. The buffered composition and labeled reactant can be supplied in a diagnostic test kit. The hydroxamic acid or acyl hydrazine can be represented by the structure(I):

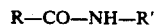

R—CO—NH—R' wherein R is aryl or 6 to 10 carbon atoms in the aromatic nucleus, alkyl of 1 to 7 carbon atoms, cycloalkyl of 5 to 10 carbon atoms in the ring, or heterocyclyl of 5 to 10 atoms in the ring, at least one of which is an oxygen, nitrogen or sulfur atom, and R' is hydroxy or amino.

9 Claims, No Drawings

WASH COMPOSITION CONTAINING SIGNAL STOP REAGENT, TEST KIT AND METHOD OF USE WITH PEROXIDASE-LABELED SPECIFIC BINDING LIGAND

FIELD OF THE INVENTION

The present invention relates to a buffered wash composition, a diagnostic test kit and a method for the detection of a specific binding ligand using the wash composition and a peroxidase-labeled specific binding reactant. It also relates to novel acyl hydrazines useful as signal stop reagents.

BACKGROUND OF THE INVENTION

There is a continuous need in medical practice, research and diagnostic procedures for rapid, accurate and qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, dental plaque, gingival crevicular fluid and other biological specimens has to be determined in an accurate and rapid fashion for suitable diagnosis or treatment.

To provide such determinations, various methods have been devised for isolating and identifying biological substances employing specific binding reactions between the substance to be detected (identified herein as a "specific binding ligand") and a compound specifically reactive with that substance (sometimes identified as a "receptor" for the ligand).

The complex formed between ligand and receptor can be detected by a variety of known methods. The most commonly used methods employ a signal generating moiety of some type which is either already attached to one of the components of the complex, or becomes part of the complex through further reaction. For example, in the formation of a complex of biotin with avidin, the complex may be detected using a label on either the avidin or biotin molecule. Such a label can be a radioisotope or an enzyme conjugated with the avidin or biotin. Alternatively, the avidinbiotin complex might be detected by further reaction with a labeled molecule which is specific to either or both parts of the complex. It is commonly known to do the same with antigens and their corresponding antibodies.

Preferred labels in specific binding reactions are clearly enzymes because the handling and disposal problems associated with radioisotopes can be avoided. Many enzymes are known to be useful in this context with peroxidases being the most common.

In diagnostic tests designed to be rapid and easy to use with moderate training in a doctor's office or clinic, the specific binding ligand of interest (such as an antigen from an infectious agent) is often detected using colorimetric, fluorescent or chemiluminescent signals resulting from reaction of the enzyme label with its corresponding substrate. There is a need to produce the signal quickly and intensely if the ligand is present.

However, there is also a need to have the signal produced in a defined region of a test zone in a test device so an adjacent or surrounding region could be used as a background control. In such cases, production of the signal should be modulated or stopped after a certain period of time in order to provide clear distinction between test zone and background zone.

It is well known that sodium azide can be used to stop the production of detectable signal when peroxidase is used as a label in specific binding reactions. However, the use of sodium azide has problems associated with it, namely incomplete signal inhibition, toxicity and its explosive nature.

An advance in the art is provided by the invention described and claimed in copending U.S.S.N. 773,063 (filed on even date herewith by Contestable, Boyer, Snyder and Kissel) and entitled "Diagnostic Test Kit and Specific Binding Assay Using Modulator of Signal Resulting from Peroxidase Label". Our colleagues found that benzohydroxamic acid and similar compounds can effectively stop the formation of detectable signal if the acid is contacted with the specific binding complex after signal-producing reagents have been added. This advantageously avoided the use of sodium azide for this purpose.

We found, however, that in the development of certain very rapid specific binding assays, such as a sandwich assay for Streptococcus A, certain additional improvements were needed. In particular, we found that the time needed to add the acid as a "signal stop" reagent at the end made the assay undesirably long so that customer satisfaction was diminished. Moreover, we observed that the assay continued to show "false positive" signals from continued signal production if a "signal stop" reagent is not added.

Further still, in the highly competitive field of immunoassays designed for doctors' offices, there is a need to reduce the number of assay steps and reagents as much as possible to reduce operator error, assay cost and waste. It was considered important to eliminate the use of a "signal stop" reagent at the end of the assay if possible.

SUMMARY OF THE INVENTION

We have found solutions to all the foregoing problems without sacrificing assay sensitivity with a method for the determination of a specific binding ligand comprising:

A. reacting a specific binding ligand from a biological specimen with a water-soluble receptor specific for the ligand, the receptor being labeled with peroxidase, to form a peroxidase-labeled specific binding complex between the ligand and receptor, B. prior to, simultaneously with or subsequently to step A, insolubilizing the specific binding ligand so as to provide a water-insoluble specific binding complex, C. washing the complex with a buffered composition to remove uncomplexed materials, the buffered composition comprising a nonionic or anionic surfactant and at least about 0.001 weight percent of a compound having the structure (I):

R—CO—NH—R' or an equivalent salt thereof, wherein R is aryl of 6 to 10 carbon atoms in the aromatic nucleus, alkyl of 1 to 7 carbon atoms, cycloalkyl of 5 to 10 carbon atoms in the ring or aromatic heterocyclyl of 5 to 10 atoms in the ring at least one of which is an oxygen, nitrogen or sulfur atom, and R' is hydroxy or amino, D. contacting the washed complex with a composition for providing a colorimetric, fluorescent or chemiluminescent signal in response to peroxidase in the complex, and E. detecting the signal as a determination of the specific binding ligand.

This invention also provides a diagnostic test kit comprising, separately packaged:

(a) a buffered composition comprising a nonionic or anionic surfactant and at least about 0.001 weight percent of a compound having the structure (I):

or an equivalent salt thereof, wherein R is aryl of 6 to 10 carbon atoms in the aromatic nucleus, alkyl of 1 to 7 carbon atoms, cycloalkyl of 5 to 10 carbon atoms in the ring or aromatic heterocyclyl of 5 to 10 atoms in the ring at least one of which is an oxygen, nitrogen or sulfur atom, and R' is hydroxy or amino, and (b) a water-soluble, peroxidase-labeled specific binding species.

Further, a buffered composition consists essentially of a nonionic or anionic surfactant, and at least about 0.001 weight percent of a compound having the structure (I):

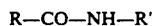

or an equivalent salt thereof, wherein R is aryl of 6 to 10 carbon atoms in the aromatic nucleus, alkyl of 1 to 7 carbon atoms, cycloalkyl of 5 to 10 carbon atoms in the ring or aromatic heterocyclyl of 5 to 10 atoms in the ring at least one of which is an oxygen, nitrogen or sulfur atom, and R' is hydroxy or amino.

Certain novel acyl hydrazines are useful as stop reagents in the practice of this invention. These compounds are generally represented by the structure (II):

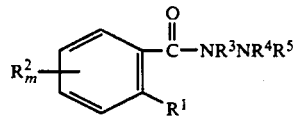

wherein m is an integer of 0 to 4, and $R^1$ is carboxylate salt, carbamoyl or N-substituted carbamoyl, $R^2$ is amino, nitro, alkyl, hydroxy, carbamoyl, N-substituted carbamoyl, a carboxylate salt or alkoxy, and $R^3$, $R^4$ and $R^5$ are independently hydrogen, alkyl or phenyl.

The present invention provides a very rapid assay for a specific binding ligand whereby a signal is quickly produced and stopped when desired for evaluation. Continuing production of signal is substantially reduced so that "false positive" signals are eliminated. The number of steps and reagents necessary for the assay are reduced, simplifying the assay and reducing costs and possibilities for error.

These advantages are achieved by using a specific hydroxamic acid or acyl hydrazine as part of a wash solution used to separate uncomplexed materials from the specific binding complex. Heretofore, it was thought that the "signal stop" reagent had to be used at the end of the assay, that is, after addition of signal-producing reagents. We have found unexpectedly that it can be added earlier in the wash solution. Apparently, sufficient "signal stop" reagent remains with the specific binding complex so that it effectively stops production of signal after a short period of time, for example after about three minutes from the time the signal producing reagents are added.

DETAILED DESCRIPTION OF THE INVENTION

The compounds used in the practice of this invention to stop the production of detectable signal are hydroxamic acids or acyl hydrazines represented by the following structure (I):

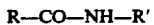

or an equivalent salt thereof wherein R' is hydroxy or amino. When R' is hydroxy, these compounds can also be in the form of hydroximic acids [that is, R—C(=NOH)—OH], and can exist in two tautomeric forms.

In this structure, R can be substituted or unsubstituted aryl of 6 to 10 carbon atoms in the aromatic nucleus, including but not limited to phenyl, naphthyl, tolyl, o-, m- or p-methoxyphenyl, o-, m- or p-hydroxyphenyl, 3-(or 6-)amino-2-carbamoylphenyl, 2-carbamoyl-3-(or 6-)nitrophenyl, a 2-carboxy-3-(or 6-)nitrophenyl metal or ammonium salt, and a 3-(or 6-)amino-2-carboxyphenyl metal or ammonium salt. When R is aryl, it is preferably phenyl, 3-(or 6-)amino-2-carbamoylphenyl or a 3-(or 6-)amino-2-carboxyphenyl metal or ammonium salt, and most preferably phenyl. Useful cations for the metal salts include, but are not limited to, alkali metal cations (such as lithium, sodium and potassium).

However, R can also be substituted or unsubstituted alkyl of 1 to 7 carbon atoms, including but not limited to methyl, ethyl, isopropyl, butyl, pentyl, hexyl, 2-methylpentyl and heptyl, or substituted or unsubstituted cycloalkyl of 5 to 10 carbon atoms in the ring, including but not limited to, cyclopentyl, cyclohexyl and cycloheptyl. R can also be an unsubstituted or substituted aromatic heterocyclyl of 5 to 10 atoms (at least one of which is oxygen, sulfur or nitrogen and the remainder being carbon atoms) in the aromatic ring. The primary heterocyclyl ring can also have carbocyclic or heterocyclic rings fused to it. Useful aromatic heterocyclyl groups include, but are not limited to, pyrrolyl, pyrazolyl, imidazolyl, triazolyl, tetrazolyl, thienyl, furyl, thiazolyl, oxazolyl, benzimidazolyl, benzothiazolyl, benzoxazolyl, pyridyl, quinolyl, pyridizinyl, pyrimidyl, triazinyl, indolyl and quinoxalinyl.

Preferably, R is phenyl, substituted or unsubstituted alkyl of 1 to 4 carbon atoms, cycloalkyl of 5 or 6 carbon atoms in the ring or an aromatic heterocyclyl of 5 or 6 nuclear carbon and heteroatoms. Most preferably, R is phenyl, 3-amino-2-carbamoylphenyl or a 3-amino-2-carboxyphenyl metal or ammonium salt. Preferred compounds are benzohydroxamic acid and equivalent salts.

For all of the acids described herein, equivalent salts include, but are not limited to, ammonium salts, alkali metal salts, alkaline earth metal salts and other salts readily apparent to one skilled in the art.

The hydroxamic acids defined above can be readily prepared using known starting materials and chemical synthetic methods such as the reaction of hydroxylamine with acyl halides and other methods described, for example, by March, *Advanced Organic Chemistry: Reactions, Mechanisms and Structure*, McGraw-Hill, 1968 and later editions, Schonbaum, *J. Biol. Chem.*, 248(2), pp. 502-511, 1973 and references mentioned pp. 916-921, 1983 and references mentioned therein. Benzohydroxamic acid is available from a number of commercial sources.

The acyl hydrazines described herein can be prepared generally by condensation of an anhydride, particularly a phthalic anhydride such as 3-nitrophthalic anhydride, with hydrazine hydrate. The resulting 1,4-dioxo-5-nitrophthalazine can be hydrolyzed with base to to form the acylhydrazine monocarboxylate salt or the carbamoyl derivative. This product can then be hydrogenated in the presence of palladium on carbon. If the base employed is ammonia, the product is a carbamoyl derivative, such as N-[3-(or 6-)amino-2-carbamoylbenzoyl]hydrazine. Otherwise, the product is a monocarboxylate salt. The preparation of a specific acyl hydrazine monocarboxylate salt, namely N-[3-(or 6-)amino-2-carboxybenzoyl]hydrazine, sodium salt is described in detail below in Example 1. Other species can be similarly prepared by a skilled chemist.

Particularly useful acyl hydrazines are defined generally by the structure (II):

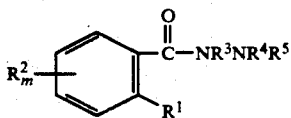

wherein m is 0 or a positive integer of 1 to 4. Preferably, m is 0, 1 or 2, and most preferably, m is 1. Additionally, in structure (II), $R^1$ is any one of the following groups: a carboxylate salt, such as sodium, potassium or ammonium carboxylate), carbamoyl and N-substituted carbamoyl (for example, substituted with methyl, ethyl, propyl, t-butyl or phenyl).

$R^2$ is amino, nitro, alkyl (preferably of 1 to 6 carbon atoms, such as methyl, ethyl, isopropyl and hexyl), substituted or unsubstituted alkoxy of 1 to 6 carbon atoms (such as methoxy, ethoxy, isopropoxy, and butoxy), hydroxy, carbamoyl, N-substituted carbamoyl (as defined above for $R^1$) and a carboxylate salt (as defined above for $R^1$). In defining $R^2$, amino is meant to include primary, secondary and tertiary amines which have substitiuents such as lower substituted or unsubstituted alkyl (1 to 6 carbon atoms, branched or linear such as methyl, ethyl, isopropyl, t-butyl, hexyl and chloromethyl), or substituted or unsubstituted phenyl (such as xylyl, tolyl and alkoxyphenyl).

Preferably, $R^2$ is amino, and most preferably, it is primary amino.

$R^3$, $R^4$ and $R^5$ are independently hydrogen, substituted or unsubstituted alkyl of 1 to 6 carbon atoms (such as methyl, ethyl, isopropyl, t-butyl, hexyl and aminomethyl) and substituted or unsubstituted phenyl (such as phenyl and xylyl). Preferably, these groups are independently hydrogen or alkyl of 1 to 3 carbon atoms, and most preferably, they are each hydrogen.

Useful compounds of structure (II) include, but are not limited to, N-[3-(or 6-)amino-2 -carboxy-benzoyl]-hydrazine, sodium salt, N-[3-(or 6-)amino-2-carboxybenzoyl]hydrazine, ammonium salt, N-[3-(or 6-)amino-2-carbamoylbenzoyl]hydrazine, N-[2-carboxy-3-(or 4-, 5- or 6-)hydroxybenzoyl]hydrazine, sodium salt, N-[2-carboxy-3-(or 4-, 5- or 6-)nitrobenzoyl]-hydrazine, potassium salt, N-[2-carboxy-3-(or 4-, 5- or 6-)methylbenzoyl]hydrazine, ammonium salt, N-[2-carboxy-3-(or 4-, 5- or 6-)isopropylbenzoyl]hydrazine, sodium salt, N-[2-carboxy-3-(or 4-, 5- or 6-)phenyl-aminobenzoyl]hydrazine, sodium salt, N-[2-carboxy-3-(or 4-, 5- or 6-)methoxybenzoyl]hydrazine, sodium salt, N-[2-carboxy-3-(or 4-, 5- or 6-)ethoxybenzoyl]-hydrazine, ammonium salt, N-(2,4,5-tricarboxybenzoyl)-hydrazine, sodium salt, N-(2,4,5-tricarbamoyl)-hydrazine, N-[2-carbamoyl-3-(or 4-, 5- or 6-)hydroxybenzoyl]hydrazine, N-[2-carbamoyl-3-(or 4-, 5- or 6-)nitrobenzoyl]hydrazine, N-[2-carbamoyl-3-(or 4-, 5-or 6-)methylbenzoyl]hydrazine, N-[2-carbamoyl-3-(or 4-, 5- or 6-)iso-propylbenzoyl]hydrazine, N-[2-carbamoyl-3-(or 4-, 5- or 6-)phenylaminobenzoyl]hydrazine, N-[2-carbamoyl-3-(or 4-, 5- or 6-)methoxy-benzoyl]hydrazine, and N-[2-carbamoyl-3-(or 4-, 5- or 6-)ethoxybenzoyl]-hydrazine.

The hydroxamic acid or acyl hydrazine described herein is provided in a buffered composition at a concentration of at least about 0.001 percent based on total solution weight. The upper limit of the amount of acid can be as high as is necessary to effectively stop the production of signal. However, in practicality, the amount reaches a point where no more acid is needed to modulate a given amount of enzyme in the assay. Generally, the amount of compound is in the range of from about 0.001 to about 0.01 weight percent, with from about 0.002 to about 0.007 weight percent being preferred. A mixture of hydroxamic acids or salts or acyl hydrazines can be used if desired. being preferred. A mixture of hydroxamic acids or salts or acyl hydrazines can be used if desired.

Generally, the hydroxamic acid or acyl hydrazine described herein is buffered to a pH of from about 6 to about 11 using one or more suitable buffers including, but not limited to, phosphate, 3-(4-morpholino)propanesulfonic acid, 2-(4-morpholino)-ethanesulfonic acid, 3-(cyclohexylamino)-1-propanesulfonic acid, 2-(N-cyclohexylamino)ethanesulfonic acid, glycine and others readily apparent to one skilled in the art. A pH in the range of from about 6.5 to about 7.5 is preferred.

A second essential component of the wash composition of this invention is an anionic or nonionic surfactant, or a mixture of either or both types of surfactants. Such surfactants are commonly used in wash compositions for specific binding assays and one skilled in the art need only to consult any of the standard literature in this field to see what surfactants might be used. A standard reference work for surfactants is *McCuthcheon's Emulsifiers and Detergents*, 1986 (or later editions), McCutcheon Division, Publishing Co., Glen Rock, N.J.

In the broadest sense of this invention, the anionic surfactant can be any water-soluble or water-dispersible compound which has a net negative charge and which has the general properties attributed to anionic surfactants.

Useful classes of anionic surfactants include, but are not limited to, carboxylate and sulfonate salts (such as alkylbenzenecarboxylates, alkylbenzenesulfonates, alkylsulfonates, sulfosuccinate ester salts, formalin condensates of naphthalene and alkylnaphthalenesulfonates), sulfate ester salts (such as alkylsulfate ester salts, polyoxyalkylene alkyl ether sulfate ester salts or polyoxyalkylene alkylaryl ether sulfate ester salts) and phosphate ester salts (such as alkyl phosphate ester salts, polyoxyalkylene alkyl ether phosphate ester salts or polyoxyalkylene alkylaryl ether phosphate ester salts). Others, including cholic acid and salts thereof (such as deoxycholate), would be readily apparent to one skilled in the art.

One useful anionic surfactant is represented by the structure (III):

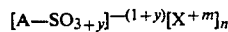

wherein A is a hydrocarbon having a molecular weight of at least about 180, $X^{+m}$ is hydrogen or a monovalent or divalent cation, m is 1 or 2, y is 0 or 1, and n is 1 or 2 provided that m and n are not both 2.

More specifically, in the noted formula, A is a linear, branched or cyclic hydrocarbon having from 13 to 18 carbon atoms, and thus a molecular weight in the range of from about 180 to about 250. Such hydrocarbon groups include, but are not limited to, linear and branched alkyl (for example, tridecyl, tetradecyl, and branched equivalents), cycloalkyl having one or more alkyl substituents (for example, cyclohexyl substituted with linear or branched $C_7$ or higher alkyls or a plurality of lower alkyls) and aromatic carbocycles having one or more alkyl substituents (for example, phenyl substituted with $C_7$ or higher alkyls). When A has more than 16 carbon atoms, it is alkylcyclyl, preferably alkylphenyl. Moreover, in such cases, the cyclyl group can be substituted with more than one alkyl. It is important that the hydrocarbon not be so large that the surfactant loses its water solubility or dispersibility.

In one embodiment, A of the noted formula is an alkyl or alkyl-substituted phenyl having a molecular weight of from about 180 to about 250. The alkyl has from 7 to 12 carbon atoms, and is linear or branched. Useful alkyl groups are, for example, n-octyl, isooctyl, n-decyl, 2,2-diethylbutyl, 2-ethyldecyl and dodecyl. A useful anionic surfactant of this embodiment is available commercially from ARCO under the trademark ULTRAWET 60L.

In another embodiment, the anionic surfactant has the noted formula above wherein A is linear or branched alkyl having from 14 to 16 carbon atoms (for example, tetradecyl, hexadecyl, 2-ethyltetradecyl and 2,2-dimethyltetradecyl). Preferably, A is tetradecyl. One useful anionic surfactant, a tetradecyl sodium sulfate, is commercially available from Union Carbide Corp. under the trademark TERGITOL 4.

Also in the foregoing formula for all preferred embodiments, m and y are both 1, and n is 2.

Generally, $X^{+m}$ is hydrogen or a monovalent or divalent cation from Groups IA or IIA of the Periodic Table, such as alkali metal ions (for example, sodium, potassium and rubidium) and alkaline earth metal ions (for example, magnesium, calcium and strontium). Alkali metal ions such as sodium and potassium ions are preferred. However, the cation can also be an ammonium or an organic cation such as trialkyl- or tetraalkylammonium ions, for example ions formed from di- and triethanolamines, such as di- and tri(2-hydroxyethyl)ammonium, and from trialkylamines, tetramethylammonium and others readily apparent to one skilled in the art, and arylammonium cations such as trimethylphenylammonium and cyclic onium cations, such as 1-methylpyridinium, 3-methylimidazolium and others readily apparent to one skilled in the art.

In a preferred embodiment of this invention, the anionic surfactant comprises an alkyl sulfate anion having from 6 to 14 carbon atoms (either linear or branched chain, for example hexyl, octyl, decyl, 2-methylhexyl, dodecyl and tetradecyl), and an alkali metal or ammonium cation.

More preferably, the sulfate anion has from 8 to 12 carbon atoms with decyl sulfate and dodecyl sulfate being most preferred. Representative alkali metal cations include, but are not limited to, lithium, sodium, potassium and rubidium. Useful surfactants include, but are not limited to, ammonium decyl sulfate, sodium dodecyl sulfate, potassium decyl sulfate, lithium hexyl sulfate and sodium tetradecyl sulfate. The corresponding acids of these compounds may also be useful. Sodium dodecyl sulfate is the most preferred compound. A mixture of anionic surfactants can be used if desired. The useful anionic surfactants can be obtained using conventional procedures, or purchased commercially.

The anionic surfactant is generally present in the wash composition in an amount of at least about 0.001 percent (based on composition weight). The upper limit of concentration is not critical and can be as high as the compounds solubility and practical considerations allow. Preferably, the amount is from about 0.5 to about 10 weight percent.

Nonionic surfactants are also well known in the art. Representative classes of nonionic surfactants useful in the practice of this invention include, but are not limited to, alkylolamides, polyoxyalkylene alkyl or alkyl aryl esters, polyoxyethylene and polyoxypropylene polyols, polyoxyalkylene fatty acid esters, polyoxyalkylene alkylamines, and polyhydric alcohol type surfactants such as polyhydric alcohol fatty acid esters. Various other useful nonionic surfactants can be understood by one of ordinary skill in the art upon consultation of the considerable literature in this field, including Japanese Kokai 58(1983)-187862 (published Nov. 2, 1938).

Particularly useful nonionic surfactants include condensation products of an alkylphenol and ethylene oxide. Preferred alkylphenols have from 1 to 20 carbons in the linear or branched alkyl group on the phenol. Octylphenol is most preferred. Generally, these compounds have from 5 to 35 ethylene oxide groups. Preferably, they have from 7 to 15 ethylene oxide groups. These nonionic surfactants are readily prepared using known procedures and starting materials, but many are also commercially available, such as NONIDET ™ P-40 (Calbiochem).

Other useful nonionic surfactants include, but are not limited to, polyoxyethylene ethers such as those sold under the mark TRITON (Rohm and Haas), for example TRITON ™ X-100 and TRITON ™ N101, or under the mark BRIJ (ICI Americas, Inc.), polyoxyethylenesorbitan derivatives such as those sold under the mark TWEEN (ICI Americas, Inc.) for example TWEEN ™ 20, and polyglycol ethers such as those sold under the mark TERGITOL ™ (Union Carbide) for example TERGITOL ™ NPX and TERGITOL ™ NP-7.

The amount of nonionic surfactant useful in the practice of the invention can be the same or different than that of the anionic surfactant described above. Preferably, the amount is from about 0.5 to about 10 weight percent.

The buffered compositions of this invention can be used as wash solutions in specific binding assays, and can include optional components such as nonimmunoreactive proteins such as serum proteins, casein and other milk proteins, fibrinogen and others readily apparent to one skilled in the art. The compositions can also include preservatives if desired.

The buffered composition of this invention can be prepared merely by mixing the anionic or nonionic surfactant, hydroxamic acid or acyl hydrazine and optional components in a suitable buffer. It can be used immediately in an assay, or stored in a suitable container for later sale or use, for example as part of a diagnostic test kit.

Such kits can include, in individual packaging or containers, the buffered composition and a water-soluble, peroxidase-labeled specific binding species (such as a receptor for the specific binding ligand of interest). Other components of a kit can include detection means such as dye providing compositions (described in more detail below), assay devices, extraction compositions, insolubilizing reagents (described below), instructions, pipettes and other apparatus needed for a typical assay. In a preferred embodiment, the kit additionally includes a disposable test device (described below), and a receptor (for example, an antibody) for the ligand which is immobilized on a particulate substrate, membrane (including polymeric and cellulosic filters), cellulosic sheet or polymeric film. Such a kit can be assembled and sold with all components present, or provided as individual parts prior to use in an assay.

The present invention provides a buffered composition and diagnostic test kit that can be used in any specific binding assay whereby a ligand of interest is complexed with its corresponding receptor, and uncomplexed materials are removed by washing prior to complex detection. Ligands which can be so complexed are well known in the art and include, but are not limited to, antigenic proteins and carbohydrates, toxins, lectins, drugs, enzymes, steroids, vitamins, polysaccharides, glycolipids, alkaloids, microorganisms, viruses, protozoa, haptens, antibodies, avidin and its derivatives, biotin and its derivatives, nucleic acids, amino acids, peptides, polypeptides, glycopeptides and any components of the foregoing materials. Preferably, this invention is used in the detection of immunological materials which are defined herein as materials, which when injected into an immunocompetent host, will produce an immunological response (that is, cause the production of antibodies specific to those materials), as well as the antibodies so produced.

More preferably, the method is useful for the determination of a hormone, drug, a bacterial or viral antigen or an antibody. Most preferably, it is useful for the determination of Streptococcus A by detecting an extracted antigen of that microorganism.

The method to detect a ligand of interest can be used to assay any human or animal biological fluid or specimen of interest including, but not limited to, whole blood, plasma, sera, lymphatic fluid, bile, urine, spinal fluid, seminal fluid, vaginal secretions, sputum, perspiration, throat specimens, human milk, stool specimens, fluid preparations of tissues, periodontal tissue, dental plaque, crevicular fluid and saliva.

It is to be understood that while the remaining discussion is directed to the determination of Streptococcus A microorganisms, the use of the kit and buffered composition is not so limited. Rather, the following discussion directed to Streptococcus A is provided merely for exemplification.

The method of this invention is generally qualitative although the amount of specific binding complex can be observed and correlated to the amount of ligand in a specimen. Thus, the assay can be quantitative also. While the ligands to be determined can be intact microorganisms, it is preferred to extract the ligand (for example, a lipopolysaccharide, capsule antigen or outer membrane protein) of interest from the host organism. Extraction can be carried out using physical or chemical means including the use of surfactants and sonication.

For assays of Streptococcus A, extraction can be carried out using any of a number of conventional procedures including the use of hot formamide, autoclaving in the presence of HCl, use of various enzymes (as described in U.S. Pat. No. 4,618,576, issued Oct. 21, 1986 to Rosenstein et al), or by the generation of nitrous acid according to U.S. Pat. No. 4,673,639 (issued Jun. 16, 1987 to Slifkin) and U.S. Pat. No. 4,808,524 (issued Feb. 28, 1989 to Snyder et al).

If desired, the extracted ligand can be removed from the original specimen, or the original specimen can be suitably diluted with buffer or water, or filtered in order to remove extraneous matter and to facilitate complexation of ligand with receptor in the assay.

The complexation of ligand and water-soluble receptor specific for the ligand provides a peroxidase-labeled specific binding complex. To accurately detect this complex in order to correlate the amount of complex with the amount of ligand, the complex must be separated from uncomplexed materials and any other materials not of interest. Separation necessitates that the specific binding ligand to be detected is insolubilized in some manner. This insolubilization can occur prior to, simultaneously with or subsequently to the complexation of ligand with peroxidase-labeled receptor therefor.

For example, the ligand can be insolubilized by direct binding to a water-insoluble substrate such as a particulate substrate (for example, polymeric or glass particles), filtration membranes, cellulosic filter papers, solid polymeric or resin-coated films, glass slides or walls of test tubes, glass or polymeric cuvettes and other substrates readily determinable by one of ordinary skill in the art. Such assays are generally known in the art as "direct binding" assays whereby the ligand directly binds to the substrate, and receptors are used to complex with the insolubilized ligand. Detection of the complex can be effected after washing using techniques described below. Further details of how direct binding assays are carried out are provided for example in U.S. Pat. No. 4,497,899 (issued Feb. 5, 1985 to Armstrong et al).

A preferred embodiment of this invention is an immunometric or sandwich assay in which the extracted ligand (for example, an antigen) is reacted at two epitopic sites with two receptor molecules (for example, two antibodies), one of which is detectably labeled with peroxidase, and the second being immobilized (or capable of being immobilized such as through avidin-biotin complexation or other specific binding reactions). Suitable substrates on which one receptor is immobilized include those noted above for direct binding assays. Preferably, particulate carrier materials formed from organisms, natural or synthetic polymers, glass, ceramics, diatomaceous earth or magnetizable particles are used. These particles are more preferably polymeric, spherical in shape and have an average particle size (in largest dimension) of from about 0.01 to about 10 $\mu$meters, although the size, structural and spatial configurations are not critical. The general procedures for immunometric assays are described, for example, in U.S. Pat. No. 4,376,110 (issued Mar. 8, 1983 to David et al) and U.S. Pat. No. 4,486,530 (issued Dec. 4, 1984 to David et al).

The receptor molecules can be attached to particulate carrier materials to form water-insoluble immunological reagents by physical or chemical means, including adsorption or covalent reaction with reactive groups on the surface of the materials. Covalent attachment is preferred for better assay reproducibility and reagent keeping. Many useful reactive groups are known in the art for attachment, which groups can be part of the chemical structure of the carrier material, or added by coating or chemical treatment of an inert material. One skilled in the art would readily understand how to prepare such materials to have any of the following reactive groups: carboxy, 2-substituted ethylsulfonyl, vinylsulfonyl, epoxy, aldehyde, active halo atoms, amino, hydrazide and active esters such as succinimidoxycarbonyl.

Particularly useful particulate carrier materials are polymeric beads described, for example, in EP-A-0 323 692 (published Jul. 12, 1989) which are prepared from one or more ethylenically unsaturated polymerizable monomers having an active halo atom, activated 2-substituted ethylsulfonyl or vinylsulfonyl groups. Other particularly useful particles having reactive carboxy groups are described for example in copending U.S.S.N. 654,112 (filed Feb. 12, 1991 by Ponticello et al) Pat. # 5,149,737.

Homo- and copolymers useful herein include the following representative materials: poly(m & p-chloromethylstyrene), poly(styrene-co-m & p-chloromethylstyrene-co-2-hydroxyethyl acrylate) (67:30:3 molar ratio), poly[styrene-co-m & p-(2-chloroethylsulfonylmethyl)styrene](96:4 molar ratio), poly{styrene-co-N-[m & p-(2-chloroethylsulfonyl-methyl)-phenyl]acrylamide}(99.3:0.7 molar ratio), poly(m & p-chloromethylstyrene-co-metharylic acid) (95:5 molar ratio), poly[styrene-co-m & p-(2-chloroethylsulfonyl-methyl)styrene-co-methacrylic acid](93.5:4.5:2 molar ratio), poly[styrene-co-3-(p-vinylbenzylthio)propionic acid](97.6:2.4 molar ratio) and poly[styrene-co-4-(2-chloroethylsulfonylmethyl)-styrene](95.5:4.5 molar ratio).

Procedures for attaching receptor molecules such as antibodies to particles having reactive groups are well known, as described for example in U.S. Pat. No. 3,925,157 (issued Dec. 9, 1975 to Hamsher), U.S. Pat. No. 4,181,636 (issued Jan. 1, 1980 to Fischer), U.S. Pat. No. 4,703,018 (issued Oct. 27, 1987 to Craig et al) and EP-A-0 323 692. In general, the antibodies are mixed with the particles under suitable conditions depending upon the attachment form (adsorption, covalent or use of a linking group). A worker skilled in the art would readily know what conditions should be used for each procedure. For example, for attachment to particles having reactive halo atoms, activated 2-substituted ethylsulfonyl or vinylsulfonyl groups, the antibodies are generally mixed with the particles for up to 24 hours at a temperature of from about 20° to about 40° C. in a suspension buffered at a pH of from about 7 to about 10. If carboxy groups are used for attachment, the well known carbodiimide activators can be used, as well as carbamoylonium compounds which are described in EP-A-0 308 235 (published Apr. 22, 1989). Antibodies can be absorbed on particles by incubating particles and antibodies in suspension at suitable temperature for several hours.

Preferably, the reagents formed from receptor and polymeric particle described above are coated or deposited on a microporous filtration membrane which is inert to chemical or biological reactions. It is generally composed of one or more natural or synthetic substances which have sufficient integrity for reagents to react or be affixed thereto without loss of form or function. It is porous enough for filtration needed to remove substantially all uncomplexed materials from the specific binding complexes formed thereon. Useful membrane materials include, but are not limited to, porous natural or synthetic polymers, sintered glass, membranes of glass or polymeric films or fibers, ceramic materials, cellulosic materials and particulate structures composed of beads bound together with an adhesive or binder material. The membranes are generally flat, but some irregularities in the surfaces are acceptable, as well as some curvature if it is desired. One skilled in the art would be able to identify other useful materials which are commercially available or prepared using known techniques. Particularly useful materials are treated or untreated polyamide microporous membranes such as those commercially available from Pall Corp. under the trademarks LOPRODYNE and BIODYNE.

The membrane generally has an average pore size in the largest dimension of from 0.5 to about 5 $\mu$meters, although smaller or larger pores would be acceptable as long as the complexes formed remain on the membrane and fluid drainage is not adversely affected.

If desired, the membrane can be coated with surfactant or nonimmunoreactive protein (such as casein or succinylated casein), as known in the art to reduce non-specific interactions or to promote desired filtration. Particularly useful membranes are described, for example, in U.S.S.N. 206,236 (filed Jun. 13, 1988 by Snyder et al) now Pat. #5,094,962 corresponding to EP-A-0 347 137 (published Sept. 12, 1990).

The reagents having appropriate receptor molecules can be affixed to the membrane over its entire surface or in defined regions thereof. Affixation is accomplished using any mechanical means such as coating, dipping, printing or spraying or fixed by covalent means. Generally, they are coated and dried on the membrane prior to use. They can be used in admixture with hydrophilic binders to provide additional integrity to the coating.

The membrane can be hand held in the assay to provide sites for complexation of ligand and the receptor thereon. However, preferably, the membrane is disposed or mounted in a disposable test device or article having a suitable frame and structure for holding the membrane and fluid which is drained therethrough. Many such test devices are known in the art, including but not limited to those shown in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike), U.S. Pat. No. 4,446,232 (issued May 1, 1984 to Liotta), U.S. Pat. No. 4,833,087 (issued May 23, 1989 to Hinckley), U.S. Pat. No. 4,847,199 (issued Jul. 11, 1989 to Snyder et al), U.S. Pat. No. 4,921,677 (issued May 1, 1990 to Hinckley et al) and U.S. Pat. No. 4,923,680 (issued May 8, 1990 to Nelson). Particularly useful test devices are those marketed by Eastman Kodak Company under the trademark SURECELL.

Preferred test devices have three test wells designed for providing both negative and positive control results as well as a specimen test result. Each test well contains a membrane as described herein.

Once the water-insoluble complex of ligand and receptor is formed (preferably on the membrane), the complex is washed with the buffered composition of this invention to remove uncomplexed materials prior to detection of the complex. If the complex is on a substrate that does not allow fluid drainage, the uncomplexed materials and fluid can be decanted off or otherwise removed. Where a membrane or filter is used, the fluid and uncomplexed materials flow through the membrane or filter and the complex of interest is left thereon. Alternatively, the uncomplexed materials can be removed by centrifugation and the pellet from that process washed with the buffered composition of this invention.

The water-insoluble complex can then be detected using a number of standard reagents, equipment and methods. For the peroxidase label, there are various known compositions which provide detectable colorimetric, fluorometric or chemiluminescent signals in response to that enzyme (through one or more reactions). For example, one preferred embodiment utilizes a dye-providing composition which provides a dye in the presence of the enzyme through one or more chemical reactions, as described for example in U.S. Pat. No. 5,024,935 (issued Jun. 18, 1991 to McClune et al). A number of leuco dyes are known to be useful for this purpose including those described in U.S. Pat. No. 4,089,747 (issued May 16, 1978 to Bruschi) and U.S. Pat. No. 4,670,386 (issued Jun. 2, 1987 to Babb et al). A preferred dye-providing composition is illustrated in the examples below.

Alternatively, the peroxidase label can be used in one or more reactions to produce a chemiluminescent signal using luminol or equivalent reagents, such as described for example in U.S. Pat. No. 4,647,532 (issued Mar. 3, 1987 to Watanabe et al), U.S. Pat. No. 4,835,101 (issued May 30, 1989 to Kao et al), U.S. Pat. No. 4,729,950 (issued Mar. 8, 1988 to Kricka et al) and U.S. Pat. No. 4,598,044 (issued Jul. 1, 1986 to Kricka et al).

The signal so produced is indicative for the determination of the specific binding ligand of interest. This signal can be directly correlated therewith using standard equipment, methods and computations.

Positive or negative controls can be carried out simultaneously with assay of the specimen.

While the method of this invention can be carried out over any suitable period of time and at any suitable temperature, in most cases, it is generally accomplished within five minutes at a temperature in the range of from about 15° to about 30° C. More preferably, the method is carried out within about three minutes, and a two minute assay is most preferred.

In a preferred method for the determination of Streptococcus A, the method comprises the steps of:

A. contacting an aqueous specimen suspected of containing an antigen extracted from Streptococcus A with a microporous filtration membrane having thereon, a water-insoluble reagent comprising water-insoluble particles having affixed thereto antibodies specific to the Streptococcus A antigen, to form, on the membrane, a water-insoluble complex between the antibody and the antigen, B. contacting the water-insoluble complex with a peroxidase labeled second antibody specific to the Streptococcus A antigen to form a peroxidase labeled, water-insoluble sandwich complex on the membrane, C. simultaneously or subsequently to step B, separating uncomplexed materials from the labeled, water-insoluble sandwich complex by washing the uncomplexed materials through the membrane with the buffered composition of this invention, to separate uncomplexed materials from the peroxidase labeled, water-insoluble sandwich complex, and D. contacting said washed complex with a composition for providing a colorimetric signal in response to peroxidase in the complex, and E. detecting the signal as a determination of Streptococcus A in the specimen.

The following examples are included to illustrate the practice of this invention, and are not meant to be limiting in any way. All percentages are by weight unless otherwise noted.

Materials and Methods for Examples

SURECELL TM disposable test devices were used containing LOPRODYNE TM nylon microporous filtration membranes (5 μmeters average pore size) incorporated into the three test wells. The membrane was used without any further treatment. Each test device contained three test wells.

A dye-providing composition A was prepared to include 4,5-bis(4-methoxyphenyl)-2-(3,5-dimethoxy-4-hydroxyphenyl)imidazole leuco dye (0.005%), poly(vinyl pyrrolidone) (1%), sodium phosphate buffer (10 mmolar, pH 6.8), hydrogen peroxide (10 mmolar), 4'-hydroxy-acetanilide (5 μmolar) and diethylenetriaminepentaacetic acid (10 pmolar).

Affinity purified rabbit polyclonal antibodies to the Group A carbohydrate antigen of Streptococcus A (Western States Plasma, Los Angeles, Calif.) were covalently bound to particles (1.4 μm average diameter) of poly[styrene-co-3-(p-vinylbenzylthio)propionic acid](97.6:2.4 molar ratio) using either o-(1H-benzotriazol-1-yl)-N,N,N',N'-tetramethyluronium tetrafluoroborate (Fluka, Buchs, Switzerland) or 1-(1-pyrrolidinylcarbonyl)pyridinium chloride as an activator. Antibody immobilization was quenched with bovine serum albumin in an amount equal to the weight of the polymer particles.

A suspension (2 μl) of the resulting reagent (0.9%), polyacrylamide (5%), UNITEX TM fluorescent dye (0.01%), and merthiolate preservative (0.01%) in glycine buffer (0.1 molar, pH 8.5) was deposited onto a finite area on the membrane in one of the test wells (center test well) of the test device. An identical formulation but with the addition of Streptococcus A carbohydrate (16 pg) was deposited in a second test well (positive control) of the test device.

Rabbit gamma globulins were attached to the same polymeric particles under similar conditions as described above, formulated and added to a third test well (negative control) of the test device.

A conjugate of peroxidase and the same antibodies specific to Streptococcus A antigen described above was prepared according to the procedure described by Yoshitake et al, *Eur. J. Biochem*, 101 p. 395 (1979). The conjugate (8.0 mg/l ) was mixed into a composition comprising succinylated casein (0.5%), TWEEN TM 20 nonionic surfactant (0.2%, Sigma Chemical Company), 4'-hydroxyacetanilide (0.15%), merthiolate (0.01%) in 3-(N-morpholino)propanesulfonic acid buffer (2.1%, pH 7.5).

Test solutions were formulated to contain citric acid (18 μl, 0.8 molar), sodium nitrite (145 μl, 7 molar) and 3-(N-morpholino)propanesulfonic acid buffer (145 l, 1 molar). Test solution A contained no antigen, while test solution B additionally contained Streptococcus A carbohydrate (10.2 ng/ml, Rhamnose units), the ligand to be determined.

Example 1 Preparation of N-[3-(or 6-)amino-2-carboxylbenzoyl]hydrazine, sodium salt This acyl hydrazine was prepared by the following sequence of steps:

Step 1:

To N,N-dimethylformamide (50 ml, DMF) was added 3-nitrophthalic anhydride (28 g, 0.145 mole). After ten minutes of stirring, the resulting solution was filtered. The filtrate was then stirred and cooled to $-10°$ C. while hydrazine hydrate (7 ml, 0.141 mole) was added. After stirring one hour, a gummy solid had precipitated. The reaction mixture was then heated to 35° C. and ethyl alcohol (50 ml) was added. The liquid was decanted and the remaining solid material was added to glacial acetic acid (100 ml), refluxed one hour and cooled to room temperature. The resulting solid was collected and dried (yield: 12.1 g, 40.3%). The proton NMR and mass spectral analyses were consistent with the structure of 1,4-dioxo-5-nitrophthalazine.

Step 2:

1,4-Dioxo-5-nitrophthalazine (8.5 g, 0.042 mole) from Step 1 was added to deionized water (125 ml). To the resulting suspension was added a solution (20 ml) of sodium hydroxide (1.68 g, 0.042 mole) in deionized water. The reaction mixture was stirred until dissolution of solid was complete (about 30 minutes), and then it was poured into an equal volume of ethyl alcohol and stirred until precipitation was complete. The resulting solid was filtered and dried (yield: 8 g, 70.2%). The proton NMR and mass spectral analyses were consistent with the structure of N-[2-carboxy-3-(or 6-)nitrobenzoyl]hydrazine, sodium salt.

Step 3:

N-[2-carboxy-3-(or 6-)nitrobenzoyl]hydrazine, sodium salt prepared in Step 2 (7.8 g, 0.032 mole) was added to deionized water (130 ml). To this solution was add 1 gram of 5% palladium on charcoal catalyst. The resulting mixture was hydrogenated at 500 psi (about 34.5 bars) and 30° C. for three hours. During the reaction, the pressure dropped 50 psi (about 3.45 bars) due to reaction of gaseous hydrogen. The catalyst was then removed by filtration, and the reaction mixture was concentrated to dryness with vacuum. The resulting solid was recrystallized from ethyl alcohol (yield: 5.2 g, 75.4%). Proton NMR and mass spectra analyses were consistent with the structure of N-[3-(or 6-)amino-2-carboxybenzoyl]hydrazine, sodium salt.

Example 2 Buffered Wash Composition

This example demonstrates the preparation of a buffered wash composition of this invention.

A buffered composition of this invention was prepared by mixing sodium decyl sulfate (1.7%), benzohydroxamic acid (0.005%) and thimerosal preservative (0.01%) in sodium phosphate (0.1 molar, pH 7.2).

Example 3 Assay for Streptococcus A Using Buffered Composition

Test solutions A and B (200 µl of each) were added to a single test well of individual disposable test devices containing the antibody reagent coated on the membranes thereof. The fluid was allowed to drain through the membrane. The peroxidase labeled antibody composition (80 µl) was then added to all test wells and allowed to drain through the membranes.

The buffered composition of Example 2 was used as a wash solution and added twice (300 µl each time) to the test wells and allowed to drain through the membranes. Some test devices were similarly treated with a Control wash solution which was like the composition of Example 2 except the benzohydroxamic acid was omitted. Other test devices were treated with a "high salt" wash solution comprised of sodium chloride (0.4 molar), sodium decyl sulfate (2.4%), thimerosal (0.01%) in sodium phosphate (0.1 molar, pH 7.2).

After washing, the leuco dye composition (100 µl) was added to the test wells and fluid was allowed to drain through. After one minute incubation at room temperature, the resulting dye signal on the membranes was evaluated in comparison to a color chart having values of 0 to 10 with 10 representing the highest dye density. The area of the membranes around the dyed area were evaluated for background signals. The dye signals were then evaluated a second time after five minutes incubation after the first evaluation.

The resulting data of several replicate assays are presented in Table I below. They show that use of the control and "high salt" wash solutions produced unacceptable false positive assay results, that is the appearance of dye signal with test solution A (no antigen). Such false positives did not result when the buffered composition of Example 2 was used. In addition, the use of the Example 2 composition allowed the elimination of a separate "signal stop" reagent and the time needed to use it. The overall background signals of the assay carried out according to this invention were much improved. The use of a separate step to stop the production of dye signal is avoided with this assay.

TABLE I

| Wash Solution | Antigen Concentration | Dye Signals | | | | | |
|---|---|---|---|---|---|---|---|
| | | 1 Minute Signal | | | 5 Minute Signal | | |
| | | Test Wells | | | | | |
| | | Negative | Test | Positive | Negative | Test | Positive |
| Control | 0 | 0.5E | 0/0 | 7/0 | 2.5E | 2/1 | 10/1 |
| | | 0.5E | 0/0 | 7/0 | 4E | 3/2 | 10/1 |
| | | 0/0 | 0/0 | 7/0 | 3E | 4E | 10/1 |
| | | 0.5E | 0/0 | 8/0 | 3E | 2/0.5 | 10/1 |
| | | 0/0 | 0/0 | 8/0 | 2E | 2/1 | 10/1 |
| | | 0/0 | 0/0 | 8/0 | 2E | 1/0.5 | 10/0.5 |
| Control | 10.2 ng/ml | 1E | 4.5/0 | 9/0 | 4E | 6.5/1 | 10/0 |
| | | 0.5E | 5/0 | 8/0 | 2.5E | 7/0 | 10/0 |
| | | 0/0 | 4.5/0 | 8/0 | 2E | 6.5/1 | 10/1 |
| | | 0/0 | 4/0 | 8/0 | 2.5E | 6/0.5 | 10/0.5 |
| | | 0/0 | 4/0 | 8/0 | 2E | 6/0.5 | 10/0.5 |
| | | 0/0 | 4/0 | 8/0 | 2E | 6/0.5 | 10/0.5 |
| "High Salt" | 0 | 0.5E | 0/0 | 8/0 | 4E | 4/5 | 10/1 |

TABLE I-continued

| Wash Solution | Antigen Concentration | Dye Signals | | | | | |
|---|---|---|---|---|---|---|---|
| | | 1 Minute Signal | | | 5 Minute Signal | | |
| | | Test Wells | | | | | |
| | | Negative | Test | Positive | Negative | Test | Positive |
| | | 0.5E | 0/0 | 8/0 | 3E | 4/2 | 10/2 |
| | | 1E | 0/0 | 8/0 | 3.5E | 3/1.5 | 10/2 |
| | | 0/0 | 0/0 | 8/0 | 2E | 2/0.5 | 10/0.5 |
| | | 0/0 | 0/0 | 8/0 | 1.5E | 2.5/1 | 10/1 |
| | | 0/0 | 0/0 | 8/0 | 1.5E | 2/0.5 | 10/0.5 |
| "High Salt" | 10.2 ng/ml | 0.5E | 4/0 | 8/0 | 2.5E | 6/0.5 | 10/0.5 |
| | | 0.5E | 4/0 | 8/0 | 2E | 6/0.5 | 10/1 |
| | | 0.5E | 4/0 | 8/0 | 1E | 5.5/0 | 10/0.5 |
| Example 1 | 0 | 0.5E | 0/0 | 7/0 | 1.5E | 0.5E | 9/0.5 |
| | | 0/0 | 0/0 | 7/0 | 0.5E | 0/0 | 9/0 |
| | | 0/0 | 0/0 | 7/0 | 0.5E | 0/0 | 9/0 |
| | | 0/0 | 0/0 | 6/0 | 1.5E | 0.5E | 8/0 |
| | | 0/0 | 0/0 | 6.5/0 | 1E | 0/0 | 8/0 |
| | | 0/0 | 0/0 | 6.5/0 | 1.5E | 1E | 8/0 |
| Example 1 | 10.2 ng/ml | 0/0 | 3/0 | 6.5/0 | 1.5E | 5/0 | 8/0 |
| | | 0/0 | 3/0 | 6.5/0 | 1.5E | 5/0 | 9/0 |
| | | 0/0 | 3.5/0 | 6.5/0 | 1E | 4.5/0 | 8/0 |
| | | 0/0 | 2.5/0 | 7/0 | 1E | 5/0.5 | 9/0 |
| | | 0/0 | 3/0 | 7/0 | 1E | 5/0 | 9/0 |
| | | 0/0 | 3/0 | 7/0 | 1E | 5/0 | 9/0 |

"0/0" = First number is dot dye signal/second signal is background dye signal.
"E" = Signifies a uniform signal across the entire membrane.

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. A method for the determination of a specific binding ligand comprising:
   A. reacting a specific binding ligand from a biological specimen with a water-soluble receptor specific for said ligand, said receptor being labeled with peroxidase,
   to form a peroxidase-labeled specific binding complex between said ligand and receptor,
   B. prior to, simultaneously with or subsequently to step A, insolubilizing said specific binding ligand so as to provide a water-insoluble specific binding complex,
   C. washing said complex with a buffered composition to remove uncomplexed materials,
   said buffered composition comprising a nonionic or anionic surfactant and at least about 0.001 weight percent of a compound having the structure (I):

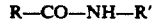

R—CO—NH—R' wherein R is aryl of 6 or 10 carbon atoms in the aromatic nucleus, alkyl of 1 to 7 carbon atoms, or cycloalkyl of 5 to 10 carbon atoms in the ring, and R' is hydroxy or amino, D. contacting said washed complex with a composition for providing a colorimetric, fluorescent or chemiluminescent signal in response to peroxidase in said complex, and
   E. detecting said signal as a determination of the presence or absence of said specific binding ligand.

2. The method of claim 8 wherein said wash composition comprises from about 0.001 to about 0.01 weight percent of said compound wherein R is phenyl, alkyl having 1 to 4 carbon atoms or cycloalkyl having 5 or 6 atoms in the ring, and R' is hydroxy.

3. The method of claim 8 wherein said signal-providing composition comprises a leuco dye which produces a dye in response to peroxidase.

4. The method of claim 8 wherein said signal-providing composition comprises luminol.

5. The method of claim 8 for the determination of a hormone, drug, bacterial or viral antigen or an antibody.

6. The method of claim 8 for the determination of Streptococcus A wherein said water-soluble receptor is an antibody specific for a Streptococcal A antigen.

7. The method of claim 8 wherein step C is carried out by washing uncomplexed materials through a microporous membrane upon which said complex is retained.

8. The method of claim 8 wherein said specific binding ligand is complexed with a water-insoluble receptor therefor prior to complexation with said labeled receptor.

9. The method of claim 8 carried out in less than about three minutes at a temperature of from about 15° to about 30° C.

* * * * *